US012797062B2

(12) United States Patent
van der Burg et al.

(10) Patent No.: US 12,797,062 B2
(45) Date of Patent: Nov. 17, 2026

(54) ANCHORING SYSTEMS AND METHODS

(71) Applicant: Siesta Medical, Inc., Los Gatos, CA (US)

(72) Inventors: Erik van der Burg, Los Gatos, CA (US); Peter Martin, Mountain View, CA (US)

(73) Assignee: Siesta Medical, Inc., Los Gatos, CA (US)

( * ) Notice: Subject to any disclaimer, the term of this patent is extended or adjusted under 35 U.S.C. 154(b) by 2 days.

(21) Appl. No.: 18/930,492

(22) Filed: Oct. 29, 2024

(65) Prior Publication Data

US 2025/0120688 A1 Apr. 17, 2025

Related U.S. Application Data

(63) Continuation of application No. 17/518,041, filed on Nov. 3, 2021, now abandoned.

(60) Provisional application No. 63/113,373, filed on Nov. 13, 2020.

(51) Int. Cl.
*A61B 17/04* (2006.01)
*A61B 17/00* (2006.01)

(52) U.S. Cl.
CPC .................... *A61B 17/0401* (2013.01); *A61B 2017/00004* (2013.01); *A61B 2017/0409* (2013.01); *A61B 2017/0417* (2013.01); *A61B 2017/0496* (2013.01)

(58) Field of Classification Search
CPC ...... A61B 17/0401; A61B 2017/00004; A61B 2017/0409; A61B 2017/0417; A61B 2017/0496; A61B 2017/0404; A61B 2017/0435; A61B 2017/0459; A61B 2017/0464
See application file for complete search history.

(56) References Cited

U.S. PATENT DOCUMENTS

| | | | |
|---|---|---|---|
| 2,143,910 | A | 1/1939 | Didusch |
| 2,167,251 | A | 7/1939 | Rogers |
| 3,194,239 | A | 7/1965 | Sullivan |
| 3,570,497 | A | 3/1971 | Lemole |
| 3,709,373 | A | 1/1973 | Aguilar |
| 4,034,763 | A | 7/1977 | Frazier |
| 4,185,626 | A | 1/1980 | Jones et al. |
| 4,235,238 | A | 11/1980 | Ogiu et al. |
| 4,372,293 | A | 2/1983 | Vijil-Rosales |

(Continued)

FOREIGN PATENT DOCUMENTS

| | | |
|---|---|---|
| FR | 2900561 | 11/2007 |
| RU | 108286 U1 | 9/2011 |

(Continued)

OTHER PUBLICATIONS

Abraham Lapidot, M.D. and Nahum Ben-Hur, M.D., Fastening the Base of the Tongue Forward to the Hyoid for Relief of Respiratory Distress in Pierre Robin Syndrome, 56 Plastic & Reconstructive Surgery 89 in 4 pages (1975).

(Continued)

*Primary Examiner* — Ryan J. Severson
(74) *Attorney, Agent, or Firm* — Knobbe, Martens, Olson & Bear, LLP

(57) ABSTRACT

Systems and methods to compress or anchor soft tissue are disclosed using one or more anchoring assemblies.

20 Claims, 18 Drawing Sheets

(56) References Cited

U.S. PATENT DOCUMENTS 4,441,497 A 4/1984 Paudler
4,448,194 A 5/1984 DiGiovanni et al.
4,557,264 A 12/1985 Hinsch
4,669,473 A 6/1987 Richards et al.
4,705,040 A 11/1987 Mueller et al.
4,741,330 A 5/1988 Hayhurst
4,792,336 A 12/1988 Hlavacek et al.
4,823,794 A 4/1989 Pierce
4,959,069 A 9/1990 Brennan et al.
5,067,955 A 11/1991 Cotrel
5,123,914 A 6/1992 Cope
5,127,413 A 7/1992 Ebert
5,176,680 A 1/1993 Vignaud et al.
5,192,303 A 3/1993 Gatturna et al.
5,250,055 A 10/1993 Moore et al.
5,304,185 A 4/1994 Taylor
5,330,488 A 7/1994 Goldrath
5,336,231 A 8/1994 Adair
5,337,736 A 8/1994 Reddy
5,342,369 A 8/1994 Harryman
5,364,407 A 11/1994 Poll
5,391,174 A 2/1995 Weston
5,411,523 A 5/1995 Goble
5,443,482 A 8/1995 Stone et al.
5,462,560 A 10/1995 Stevens
5,501,691 A 3/1996 Goldrath
5,522,846 A 6/1996 Bonutti
5,534,011 A 7/1996 Greene, Jr. et al.
5,562,685 A 10/1996 Molenauer et al.
5,620,012 A 4/1997 Benderev
5,672,316 A 9/1997 Knapp
5,692,520 A 12/1997 Lavoisier
5,702,399 A 12/1997 Kilpela et al.
5,722,981 A 3/1998 Stevens
5,868,789 A 2/1999 Huebner
5,895,395 A 4/1999 Yeung
5,906,624 A 5/1999 Wenstrom, Jr.
5,980,559 A 11/1999 Bonutti
5,988,171 A 11/1999 Sohn
6,096,051 A 8/2000 Kortenbach et al.
6,149,669 A 11/2000 Li
6,159,235 A 12/2000 Kim
6,161,541 A 12/2000 Woodson
6,258,106 B1 7/2001 Leonard
6,264,677 B1 7/2001 Simon et al.
6,273,852 B1 8/2001 Lehe et al.
6,368,326 B1 4/2002 Dakin
6,482,178 B1 11/2002 Andrews et al.
6,554,845 B1 4/2003 Fleenor et al.
6,610,080 B2 8/2003 Morgan
6,638,283 B2 10/2003 Thal
6,638,286 B1 10/2003 Burbank et al.
6,660,023 B2 12/2003 McDevitt et al.
6,672,316 B1 1/2004 Weihrauch
6,692,530 B2 2/2004 Doubler et al.
6,746,456 B2 6/2004 Xiao
6,786,913 B1 9/2004 Sancoff et al.
6,984,237 B2 1/2006 Hatch et al.
6,991,636 B2 1/2006 Rose
7,081,126 B2 7/2006 McDevitt et al.
7,090,672 B2 8/2006 Underwood et al.
7,172,595 B1 2/2007 Goble
7,213,599 B2 5/2007 Conrad et al.
7,232,448 B2 6/2007 Battles
7,237,554 B2 7/2007 Conrad et al.
7,306,613 B2 12/2007 Kawashima et al.
7,337,781 B2 3/2008 Vassallo
7,367,340 B2 5/2008 Nelson et al.
7,401,611 B2 7/2008 Conrad et al.
7,547,326 B2 * 6/2009 Bhatnagar .......... A61B 17/0682 606/220
7,625,386 B2 12/2009 Abe et al.
7,673,635 B2 3/2010 Conrad et al.
7,674,276 B2 3/2010 Stone et al.
7,703,460 B2 4/2010 Conrad et al.
7,780,730 B2 8/2010 Saidi
7,867,251 B2 1/2011 Colleran et al.
7,892,256 B2 2/2011 Grafton
7,918,868 B2 4/2011 Marshall et al.
7,993,369 B2 8/2011 Dreyfuss
8,038,712 B2 10/2011 van der Burg et al.
8,096,303 B2 1/2012 Dineen et al.
8,133,276 B2 3/2012 Saidi
8,167,787 B2 5/2012 Gillis
8,177,795 B2 5/2012 Niese et al.
8,186,355 B2 5/2012 van der Burg et al.
8,236,027 B2 8/2012 Wu
8,460,322 B2 6/2013 van der Burg et al.
8,545,535 B2 10/2013 Hirotsuka et al.
8,561,616 B2 10/2013 Rousseau et al.
8,561,617 B2 10/2013 Lindh et al.
8,784,488 B2 7/2014 Saidi
8,821,495 B2 9/2014 van der Burg et al.
8,911,347 B2 12/2014 Browning
9,386,981 B2 7/2016 van der Burg et al.
9,463,014 B2 10/2016 Feezor et al.
9,480,594 B2 11/2016 Saidi et al.
9,492,160 B2 * 11/2016 Torrie ................ A61B 17/0401
9,597,220 B2 3/2017 Gonzales et al.
9,833,353 B2 12/2017 Witt
9,877,862 B2 1/2018 Weadock
9,907,591 B2 3/2018 Overes et al.
10,004,495 B2 * 6/2018 DiMatteo ......... A61B 17/06166
10,182,810 B2 1/2019 van der Burg et al.
10,966,710 B2 4/2021 van der Burg et al.
11,039,831 B2 6/2021 Feezor et al.
11,064,991 B2 7/2021 Feezor et al.
11,185,320 B2 * 11/2021 Kaiser ................... A61F 2/0811
11,554,027 B2 1/2023 Feezor et al.
11,612,391 B2 * 3/2023 Stone ................. A61B 17/0469 606/139
11,642,123 B2 5/2023 Feezor et al.
11,672,528 B2 6/2023 van der Burg et al.
11,974,738 B2 5/2024 Feezor et al.
12,201,291 B2 1/2025 van der Burg et al.
2003/0149447 A1 8/2003 Morency et al.
2004/0134491 A1 7/2004 Pflueger et al.
2005/0092332 A1 5/2005 Conrad et al.
2005/0119696 A1 6/2005 Walters et al.
2005/0126563 A1 6/2005 van der Burg et al.
2005/0149122 A1 7/2005 McDevitt et al.
2005/0192631 A1 9/2005 Grafton
2005/0245932 A1 11/2005 Fanton
2005/0288690 A1 12/2005 Bourque et al.
2006/0036265 A1 2/2006 Dant
2006/0070626 A1 4/2006 Frazier et al.
2006/0106423 A1 5/2006 Weisel et al.
2006/0150986 A1 7/2006 Roue et al.
2006/0201519 A1 9/2006 Frazier et al.
2006/0207606 A1 9/2006 Roue et al.
2006/0207607 A1 9/2006 Hirotsuka et al.
2006/0207608 A1 9/2006 Hirotsuka et al.
2006/0207612 A1 9/2006 Jackson et al.
2006/0235264 A1 10/2006 Vassallo
2006/0247644 A1 11/2006 Bhatnagar et al.
2006/0271060 A1 11/2006 Gordon
2006/0276817 A1 12/2006 Vassallo et al.
2006/0282081 A1 12/2006 Fanton et al.
2006/0282082 A1 12/2006 Fanton et al.
2006/0282083 A1 12/2006 Fanton et al.
2006/0282088 A1 12/2006 Ryan
2007/0088391 A1 4/2007 McAlexander et al.
2007/0119463 A1 5/2007 Nelson et al.
2007/0144539 A1 6/2007 van der Burg et al.
2007/0149986 A1 6/2007 Morris et al.
2007/0149987 A1 6/2007 Wellman et al.
2007/0179509 A1 8/2007 Nagata et al.
2007/0179529 A1 8/2007 Doyle
2007/0203498 A1 8/2007 Gerber et al.
2007/0213770 A1 9/2007 Dreyfuss
2007/0225763 A1 9/2007 Zwolinski et al.
2007/0261701 A1 11/2007 Sanders
2007/0288057 A1 12/2007 Kuhnel
2008/0023012 A1 1/2008 Dineen et al.

(56) References Cited

U.S. PATENT DOCUMENTS

| | | | |
|---|---|---|---|
| 2008/0027273 | A1 | 1/2008 | Gutternman |
| 2008/0027480 | A1 | 1/2008 | van der Burg |
| 2008/0027560 | A1 | 1/2008 | Jackson et al. |
| 2008/0035160 | A1 | 2/2008 | Woodson et al. |
| 2008/0053461 | A1 | 3/2008 | Hirotsuka et al. |
| 2008/0058584 | A1 | 3/2008 | Hirotsuka et al. |
| 2008/0066766 | A1 | 3/2008 | Paraschac et al. |
| 2008/0066767 | A1 | 3/2008 | Paraschac et al. |
| 2008/0066769 | A1 | 3/2008 | Dineen et al. |
| 2008/0077161 | A1 | 3/2008 | Kaplan |
| 2008/0077162 | A1 | 3/2008 | Domingo |
| 2008/0082113 | A1 | 4/2008 | Bishop et al. |
| 2008/0091219 | A1 | 4/2008 | Marshall et al. |
| 2008/0103506 | A1 | 5/2008 | Volpi et al. |
| 2008/0154286 | A1 | 6/2008 | Abbott et al. |
| 2008/0208265 | A1 | 8/2008 | Frazier et al. |
| 2008/0275469 | A1 | 11/2008 | Fanton et al. |
| 2009/0014012 | A1 | 1/2009 | Sanders |
| 2009/0018554 | A1 | 1/2009 | Thorne et al. |
| 2009/0026236 | A1 | 1/2009 | Krause |
| 2009/0069824 | A1 | 3/2009 | Chu |
| 2009/0082788 | A1 | 3/2009 | ElMaraghy |
| 2009/0099598 | A1 | 4/2009 | McDevitt et al. |
| 2009/0105751 | A1 | 4/2009 | Zentgraf |
| 2009/0105753 | A1 | 4/2009 | Greenhalgh et al. |
| 2009/0118762 | A1 | 5/2009 | Crainch et al. |
| 2009/0125043 | A1 | 5/2009 | Dehnad |
| 2009/0210005 | A1 | 8/2009 | Dinger, III et al. |
| 2009/0216268 | A1 | 8/2009 | Panter |
| 2009/0228041 | A1 | 9/2009 | Domingo |
| 2009/0248071 | A1 | 10/2009 | Saint et al. |
| 2009/0312791 | A1 | 12/2009 | Lindh et al. |
| 2009/0318938 | A1 | 12/2009 | Hathaway et al. |
| 2009/0318958 | A1 | 12/2009 | Ochiai |
| 2009/0319046 | A1 | 12/2009 | Krespi et al. |
| 2010/0004683 | A1 | 1/2010 | Hoof et al. |
| 2010/0106169 | A1 | 4/2010 | Niese et al. |
| 2010/0114123 | A1 | 5/2010 | Nason |
| 2010/0132719 | A1 | 6/2010 | Jacobs et al. |
| 2010/0145385 | A1 | 6/2010 | Surti et al. |
| 2010/0160962 | A1 | 6/2010 | Dreyfuss et al. |
| 2010/0160963 | A1 | 6/2010 | Fallin et al. |
| 2010/0198235 | A1 | 8/2010 | Pierce et al. |
| 2010/0262184 | A1 | 10/2010 | Dreyfuss |
| 2010/0280611 | A1 | 11/2010 | Saidi |
| 2011/0004242 | A1 | 1/2011 | Stchur |
| 2011/0155142 | A1 | 6/2011 | Boucher |
| 2011/0230974 | A1 | 9/2011 | Musani |
| 2011/0245850 | A1 | 10/2011 | van der Burg et al. |
| 2011/0308529 | A1 | 12/2011 | Gillis et al. |
| 2012/0017919 | A1 | 1/2012 | Gillis et al. |
| 2012/0132214 | A1 | 5/2012 | Gillis et al. |
| 2012/0136200 | A1 | 5/2012 | Miraki |
| 2012/0277767 | A1 | 11/2012 | Powers et al. |
| 2012/0303045 | A1 | 11/2012 | Cooper et al. |
| 2013/0211451 | A1 | 8/2013 | Wales et al. |
| 2013/0233324 | A1 | 9/2013 | Witt et al. |
| 2013/0345724 | A1 | 12/2013 | van der Burg et al. |
| 2014/0074158 | A1 | 3/2014 | Feezor et al. |
| 2014/0243975 | A1 | 8/2014 | Saidi |
| 2014/0275756 | A1 | 9/2014 | Bender et al. |
| 2014/0288597 | A1 | 9/2014 | Fanton et al. |
| 2014/0288600 | A1 | 9/2014 | Yeung et al. |
| 2014/0350599 | A1 | 11/2014 | Torrie et al. |
| 2015/0012090 | A1 | 1/2015 | Saidi |
| 2015/0038992 | A1 | 2/2015 | DiMatteo et al. |
| 2015/0250470 | A1 | 9/2015 | Vargas |
| 2015/0250476 | A1 | 9/2015 | Feezor et al. |
| 2016/0038267 | A1 | 2/2016 | Allen et al. |
| 2016/0058556 | A1 | 3/2016 | Rosenthal et al. |
| 2017/0000477 | A1 | 1/2017 | van der Burg et al. |
| 2017/0020506 | A1 | 1/2017 | Feezor et al. |
| 2017/0079774 | A1 | 3/2017 | Saidi et al. |
| 2017/0105836 | A1 | 4/2017 | Baron et al. |
| 2017/0143532 | A1 | 5/2017 | Gonzales et al. |
| 2018/0021036 | A1 | 1/2018 | Kaiser et al. |
| 2019/0167264 | A1 | 6/2019 | Feezor et al. |
| 2019/0175169 | A1 | 6/2019 | van der Burg et al. |
| 2019/0343622 | A1 | 11/2019 | Rosenthal et al. |
| 2020/0054446 | A1 | 2/2020 | Rosenthal et al. |
| 2020/0078194 | A1 | 3/2020 | Feezor et al. |
| 2020/0197002 | A1 | 6/2020 | Stone et al. |
| 2021/0177398 | A1 | 6/2021 | van der Burg et al. |
| 2021/0338237 | A1 | 11/2021 | van der Burg et al. |
| 2021/0378655 | A1 | 12/2021 | Feezor et al. |
| 2022/0031300 | A1 | 2/2022 | Hoffman |
| 2022/0151603 | A1 | 5/2022 | van der Burg et al. |
| 2023/0165691 | A1 | 6/2023 | Feezor et al. |
| 2023/0233203 | A1 | 7/2023 | Feezor et al. |
| 2023/0255621 | A1 | 8/2023 | van der Burg et al. |
| 2024/0245400 | A1 | 7/2024 | Feezor et al. |
| 2025/0120688 | A1* | 4/2025 | van der Burg ..... A61B 17/0401 |
| 2025/0134518 | A1 | 5/2025 | van der Burg et al. |
| 2025/0268591 | A1 | 8/2025 | van der Burg et al. |

FOREIGN PATENT DOCUMENTS

| | | |
|---|---|---|
| WO | WO 1999/003402 | 1/1999 |
| WO | WO 2002/039905 | 5/2002 |
| WO | WO 2007/073931 | 7/2007 |
| WO | WO 2011/123714 | 10/2011 |
| WO | WO 2011/151745 | 12/2011 |
| WO | WO 2014/039848 | 3/2014 |
| WO | WO 2015/134763 | 9/2015 |

OTHER PUBLICATIONS

Beverly Douglas, M.D., The Treatment of Micrognathia Associated with Obstruction by a Plastic Procedure, in 1 Plastic & Reconstructive Surgery 300, in 12 pages (Warren B. Davis ed., The Williams & Wilkins Co. 1946).

Chris T. Oeconomopoulos, M.D., The Value of Glossopexy in Pierre-Robin Syndrome, 262 NEJM 1267 in 3 pages (1960).

Frank G. DeLuca, M.D., and Conrad W. Wesselhoeft, M.D., Surgically Treatable Causes of Neonatal Respiratory Distress, 5 Clinics in Perinatology 377 in 19 pages (1978).

H. Faye-Lund, G. Djupesland, & T. Lyberg, Glossopexia—Evaluation of a New Surgical Method for Treating Obstructive Sleep Apnea Syndrome, 492 Acta Oto-Laryngologica 46 in 4 pages (1990).

M.R. Wexler, H. Kaplan, K. Abu-Dalu, & M. Rousso, A Dynamic Fixation of the Base of the Tongue to the Mandible Using De-epithelized Tongue Flap in the Pierre Robin Syndrome, 4 Chirurgia Plastica 297 in 5 pages (1979).

Peter Randall, M.D., The Robin Anomalad: Micrognathia and Glossoptosis with Airway Obstruction, Reconstructive Plastic Surgery 2241 in 13 pages (2d ed., W.B. Saunders Co. 1977).

Robert M. Woolf, M.D., Nicholas Georgiade, M.D., and Kenneth L. Pickrell, M.D., Micrognathia and Associated Cleft Palate, 26 Plastic & Reconstructive Surgery 199 in 4 pages (1960).

Robert W. Riley, DDS, MD, Nelson B. Powell, MD and Christian Guilleminault, MD, Obstructive Sleep Apnea and the Hyoid: A Revised Surgical Procedure, 111 Otolaryngol Head Neck Surgery 717 in 5 pages (1994).

Stephen R. Lewis, M.D., John B. Lynch, M.D., & Truman G. Blocker, Jr., M.D., Fascial Slings for Tongue Stabilization in the Pierre Robin Syndrome, 42 Plastic & Reconstructive Surgery 237 in 6 pages (1968).

International Search Report dated Jun. 10, 2011 in International Patent Application No. PCT/US2011/030829 in 16 pages.

International Search Report dated Dec. 12, 2013 in International Patent Application No. PCT/US2013/058547 in 7 pages.

International Search Report/Written Opinion for application No. PCT/US2015/018944 dated Jun. 10, 2015 in 10 pages.

Search Report dated Apr. 28, 2015 in EP Patent Application No. 11763477.4 in 2 pages.

Beveled Definition and Meaning—Merriam-Webster (2023).

Blunt Definition and Meaning—Merriam-Webster (2023).

Blunt Definition—Merriam-Webster (2024).

(56) References Cited

OTHER PUBLICATIONS

English Machine Translation of Description of FR2900561A1 (Tornier) from Espacenet website <https://translationportal.epo.org/u emtp/translate/? ACTION =description-retrieval&COU NTRY= FR&ENGI N E=google&FORMAT=docdb&KI N D=A 1 &LOCALE=en_EP &NUMBER=2900561&SRCLANG=fr&TRGLANG=en> Accessed Mar. 31, 2026 (Year: 2007).

* cited by examiner

ANCHORING SYSTEMS AND METHODS

PRIORITY CLAIM

The present application is a continuation application of U.S. application Ser. No. 17/518,041 filed Nov. 3, 2021, which claims priority benefit under 35 U.S.C. § 119(e) of U.S. Provisional Patent Application No. 63/113,373 filed on Nov. 13, 2020, the disclosures of which is incorporated by reference herein in its entirety.

BACKGROUND

Field

In some aspects, the invention relates generally systems and methods to compress or anchor soft tissue. Disclosed herein are systems and methods for tissue anchoring using one or more anchoring assemblies.

Description of the Related Art

In many surgical procedures, there is a need to compress or anchor tissue.

SUMMARY

The present disclosure provides anchoring system and methods.

DETAILED DESCRIPTION

In some embodiment, disclosed herein are improved systems and methods to compress or anchor to soft tissue in a permanent or temporary way. Conventionally, T-Anchors generally serve only to anchor to a point inside tissue or adjacent to a tissue surface. The suture tails must be tied between two T-Anchors to achieve tissue compression and the anchors are not generally easily removed. A T-anchor is a medical device which has been used for moving two body walls into proximity and for maintaining those two walls in proximity for an extended period of time. The T-anchor typically includes an anchor bar having a longitudinal configuration and a tether, such as a suture attached to the bar and extending laterally from the bar. An introducer can be used to pass the anchor bar through the two walls and to deploy the anchor bar on the far side of the second wall. The suture is left to extend through the two walls, and can be provided with a bolster on the near side of the two walls which is slidable along the suture. As the suture is pulled and the bolster is pushed, the anchor bar seats against the second wall which is drawn into proximity with the first wall. A knot tied in the suture on the proximal side of the bolster maintains the anchor in this operative position with the two walls in close proximity. In some embodiments, disclosed herein are improved systems and methods that allow for removal of a placed T-Anchor. In some embodiment, when combined with a T-anchor in an assembly, the improved systems and methods allow for permanent tissue compression/apposition without the need to tie knots. Disclosed herein are figures and descriptions of some advantageous effects. In some embodiments, the systems and methods include removable T-Anchors. In some embodiments, the systems and methods include ratcheting T-Anchors. In some embodiments, the systems and methods include multi-element anchors. In some embodiments, the systems and methods include multi-element anchors that facilitate anchoring in soft tissue with barbs. In some embodiments, the systems and methods include two individual anchor elements connected by a flexible member thus allowing for significant relative movement/rotation between them. In some embodiments, the systems and methods include a variety of anchoring assemblies, wherein an anchor or anchoring assembly can include any feature of an anchor or anchoring assembly described herein.

Figure 1:
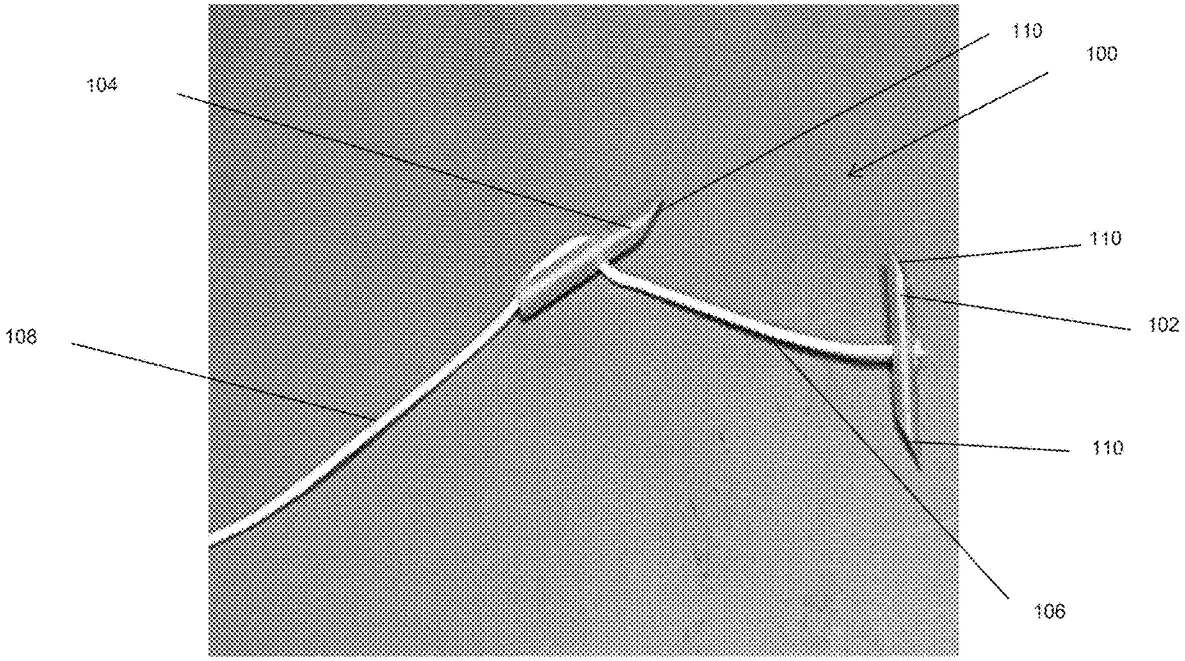
FIGS. 1-17B illustrate various embodiments of anchoring assemblies.

FIG. 1 illustrates a ratcheting T-Anchor assembly 100. The T-Anchor assembly 100 can include a first T-Anchor 102. The T-Anchor assembly 100 can include a second T-Anchor 104. In some embodiments, combining the first T-Anchor 102 with the second T-Anchor 104 can allow for improvements as described herein. The T-Anchor assembly 100 can include a length of suture 106 between the first T-Anchor 102 and the second T-Anchor 104. The length of suture 106 between the first T-Anchor 102 and the second T-Anchor 104 can be fixed. The length of suture 106 between the first T-Anchor 102 and the second T-Anchor 104 can have tension applied to it, as described herein. The length of suture 106 can be bonded to the first T-Anchor 102 and the second T-Anchor 104. The T-Anchor assembly 100 can include a suture tail 108. The T-Anchor assembly 100 can include one beveled end 110. The T-Anchor assembly 100 can include two beveled ends 110. The first T-Anchor 102 can include one beveled end 110. The second T-Anchor 104 can include two beveled ends 110. The beveled ends 110 can optimize rotation into a locked position perpendicular to the suture. In other embodiments, one or more ends can be straight, that is, non-beveled.

Figure 2:
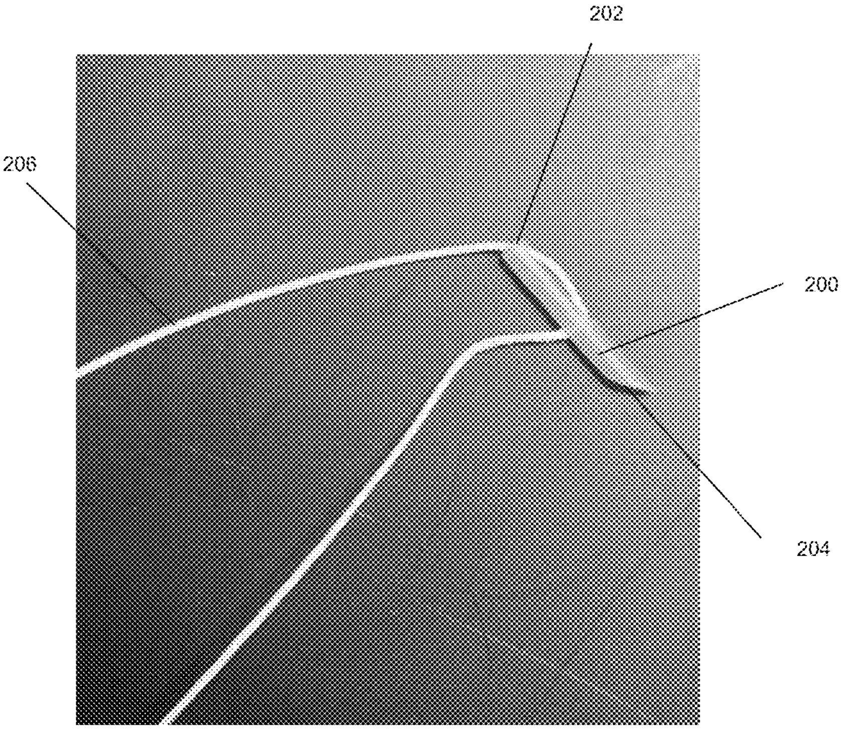

FIG. 2 illustrates a T-Anchor 200. The T-Anchor 200 can be a simple removable T-Anchor. The T-Anchor 200 can have any features described herein. The T-Anchor 200 can be used with any assembly described herein. The T-Anchor 200 can be suitable for permanent anchoring. The T-Anchor 200 can suitable for temporary anchoring. The T-Anchor 200 can be suitable for anchoring of tissue. The T-Anchor 200 can include one blunt end 202. The T-Anchor 200 can include one beveled end 204. The T-Anchor 200 can be delivered blunt end first to prevent damaging sensitive tissues such as blood vessels, organs, or mucosa. The T-anchor 200 can rotate after being delivered. The T-Anchor 200 can rotate to engage tissue with the beveled end 204. The T-Anchor 200 can engage a suture 206. The beveled end 204 can optimize rotation into a locked position perpendicular to the suture 206.

Figure 3:
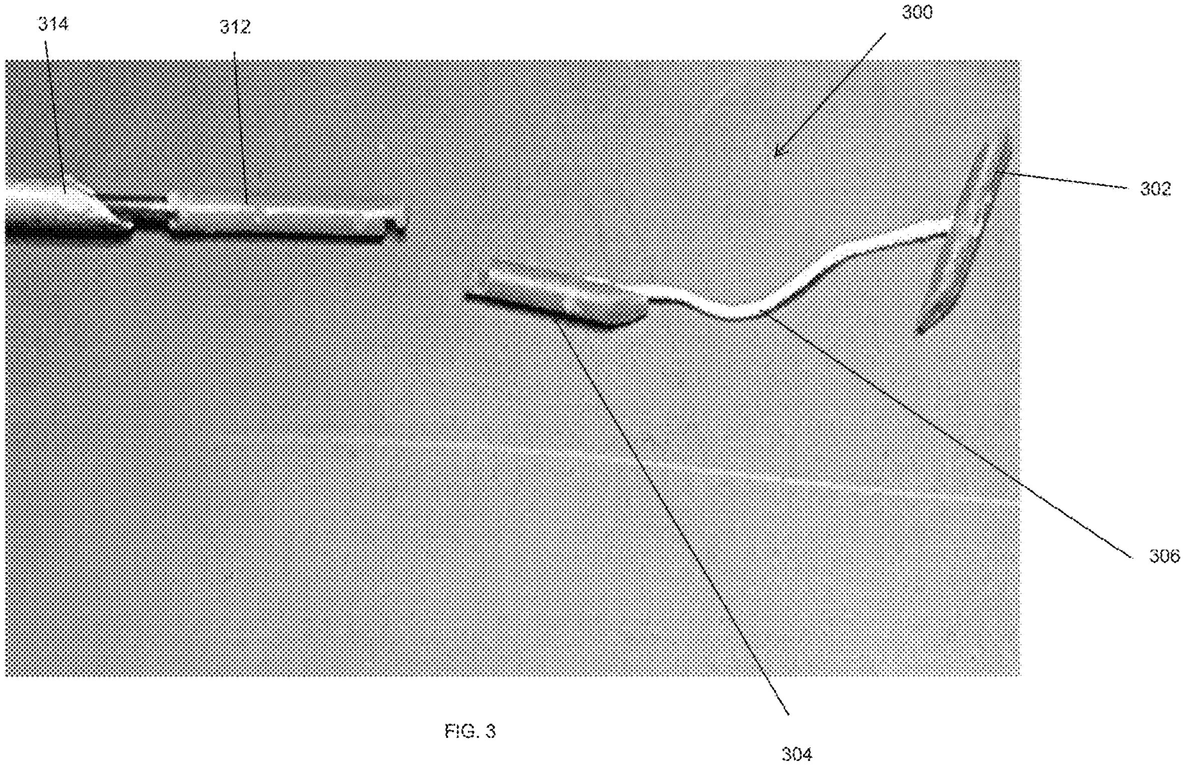

FIG. 3 illustrates a T-Anchor assembly 300. The T-Anchor assembly 300 can have any features described herein. The T-Anchor assembly 300 can be used with any assembly described herein. The T-Anchor assembly 300 can include a first T-Anchor 302. The T-Anchor assembly 300 can include a second T-Anchor 304. The T-Anchor assembly 300 can include a length of suture 306 between the first T-Anchor 302 and the second T-Anchor 304. The T-Anchor assembly 300 can include a connector 312. The connector 312 can be coupled to a delivery system 314. The connector 312 can engage and disengage the second T-Anchor 304. The connector 312 can be any mechanical connection between components. The connector 312 can include shaped, interlocking tabs. The connector 312 can include a bayonet configuration. The connector 312 can include projections. The connector 312 can include grooves. The connector 312 can include threads. The connector 302 can be between the delivery system 314 and a second T-Anchor 304. The connector 312 can be configured to apply tension before release of the second T-Anchor 304. The connector 312 can be configured to apply tension to the length of suture 306 between the first T-Anchor 302 and the second T-Anchor 304. The connector 312 can be any type of connection. The connector 312 can be on one side of the second T-Anchor 304. The connector 312 can axially pull on the second T-Anchor 304. The connector 312 can slide laterally relative to the second T-Anchor 304 to release the second T-Anchor 304. Other types of connections between the delivery system 314 and the second T-Anchor 304 are contemplated.

Figure 4:
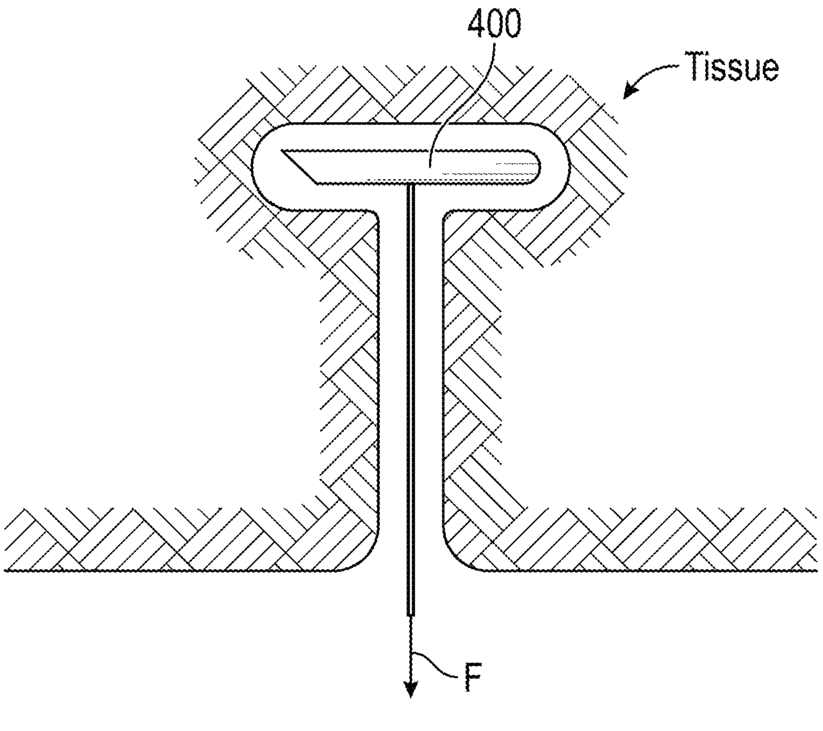

FIG. 4 illustrates a T-Anchor 400. The T-Anchor 400 can have any features described herein. The T-Anchor 400 can be used with any assembly described herein. There can be tissue and suture anchor moveability. The T-Anchor 400 is embedded in tissue. A force F is applied to the T-Anchor 400. The T-Anchor 400 can be a standard T-Anchor. This anchor engages but is not removable once delivered. In some embodiments, the T-Anchor 400 is a Kumar® T-Anchor. This limitation restricts the application of the T-Anchor 400. The improved systems and methods can have numerous applications. By incorporating a connection to one side of the anchor, the placement can be adjusted or the anchor can be removed completely.

Figure 5A:
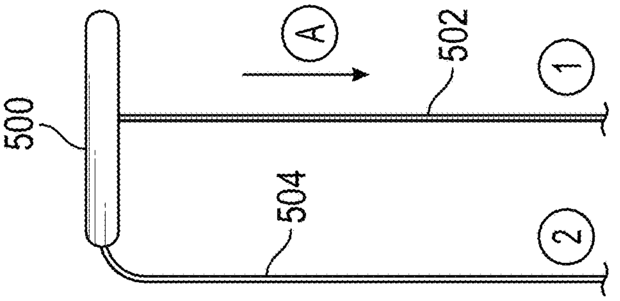
Figure 5B:
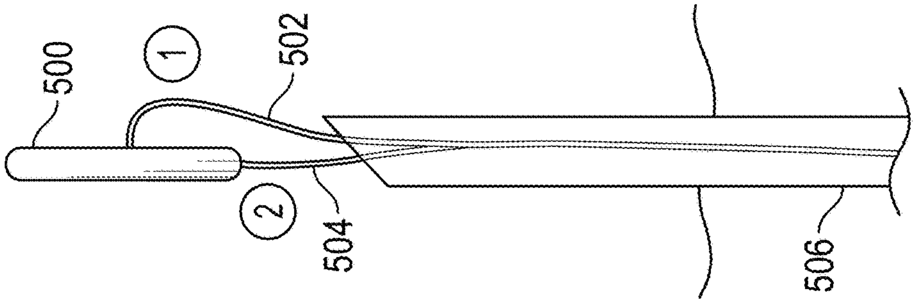

FIGS. 5A-5E illustrates methods of use of a T-Anchor 500. The T-Anchor 500 can have any features described herein. The T-Anchor 500 can be used with any assembly described herein. FIG. 5A illustrates the T-Anchor 500. The T-Anchor 500 can be coupled to two sutures. The T-Anchor 500 can be coupled to a first suture 502. The T-Anchor 500 can be coupled to a second suture 504. FIG. 5A illustrates the first suture 502 and the second suture 504 relative to the T-Anchor 500. The first suture 502 can be centrally placed relative to the T-Anchor 500. The second suture 504 can extend from an end of the T-Anchor 500. Other placements of the suture are contemplated. The first suture 502 can be fixed relative to the T-Anchor 500. The second suture 504 can be fixed relative to the T-Anchor 500. FIG. 5B illustrates the delivery of the T-Anchor 500. The T-Anchor 500 can be delivered through a hollow needle 506. The T-Anchor 500 can be delivered in tissue.

Figure 5C:
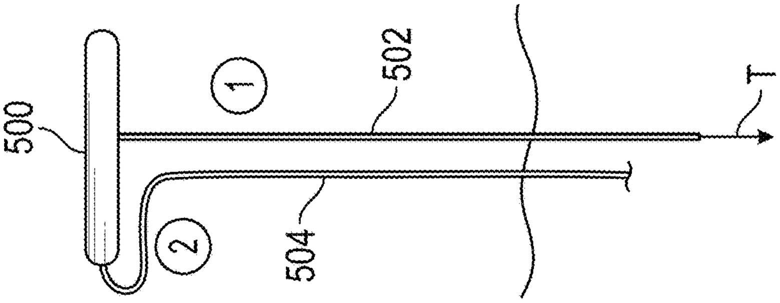
Figure 5D:
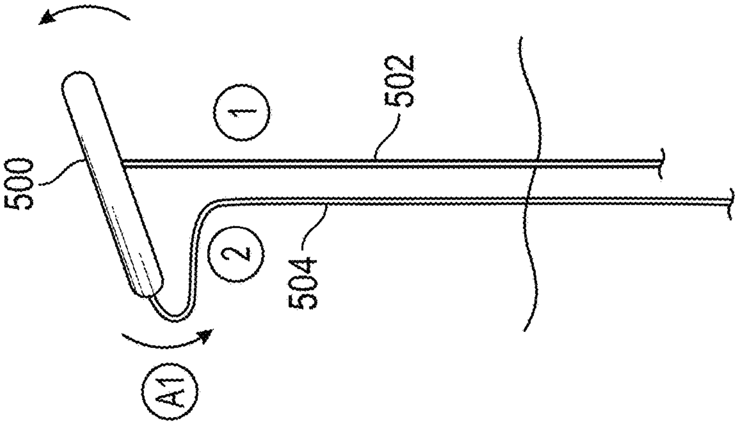
Figure 5E:
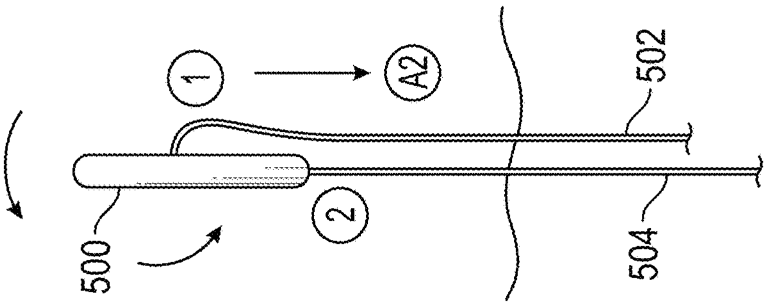

FIGS. 5C-5E illustrate methods of applying tension. When placed in tissue, pulling on the first suture 502 will lock the T-Anchor 500. When placed in tissue, pulling on the second suture 504 will re-position the T-Anchor 500, in the direction of arrow A. FIG. 5C illustrates tension on the first suture 502. This tension on the first suture 502 will lock the T-Anchor 500. FIGS. 5D and 5E illustrate tension on the second suture 504. The tension rotations the T-Anchor 500. The tension allows repositioning of the T-Anchor 500. FIGS. 5D and 5E illustrate rotation of the T-Anchor 500 counter-clockwise. The T-Anchor 500 is rotated from generally horizontal in FIG. 5D to generally vertical in FIG. 5E. The T-Anchor 500 is re-positioned to point in the direction of arrow A2. The T-Anchor 500 can re-positioned to a different orientation within the tissue by pulling the second suture 504. The T-Anchor 500 can be re-positioned for removal. In some methods, further pulling on the section suture 504 can cause removal of the T-Anchor 500.

Figure 6C:
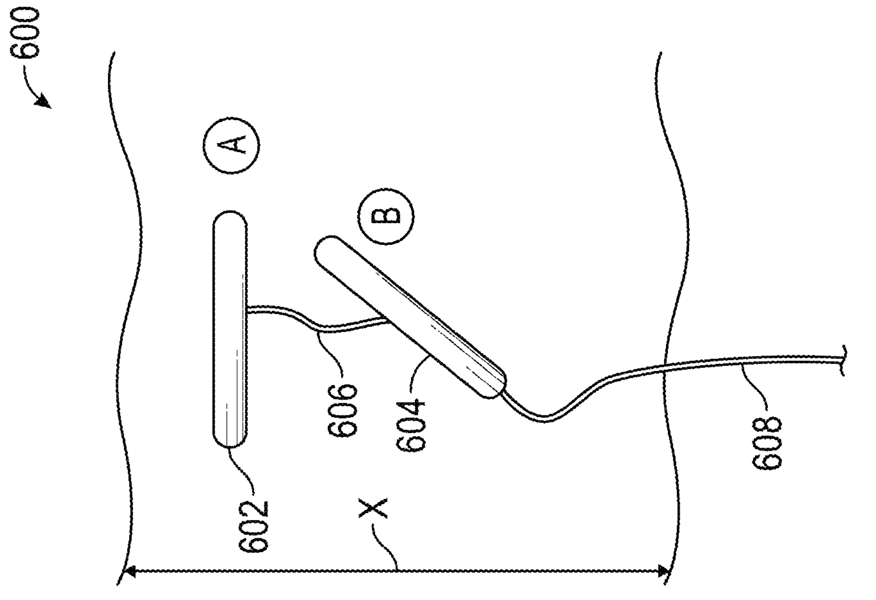
Figure 6B:
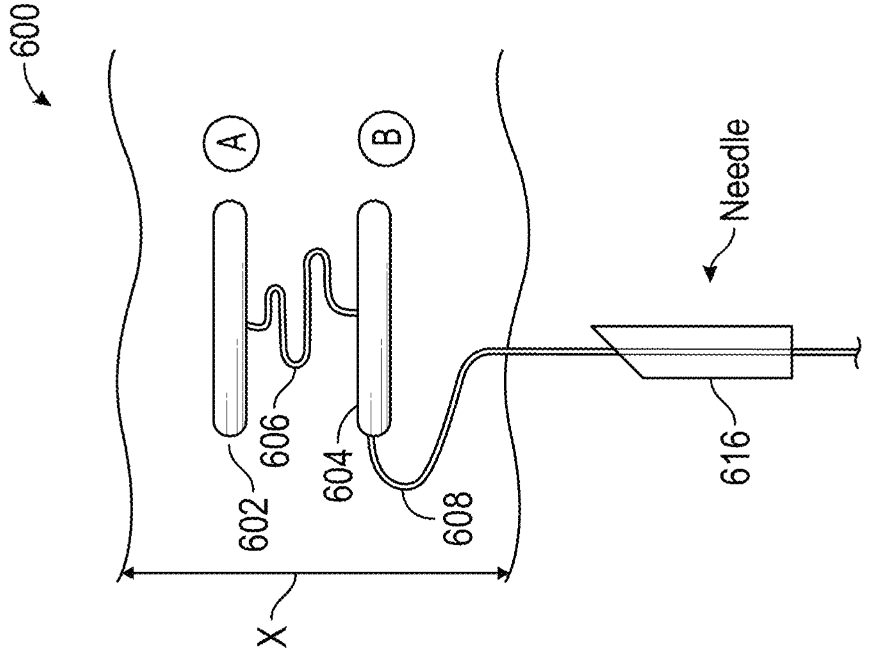
Figure 6A:
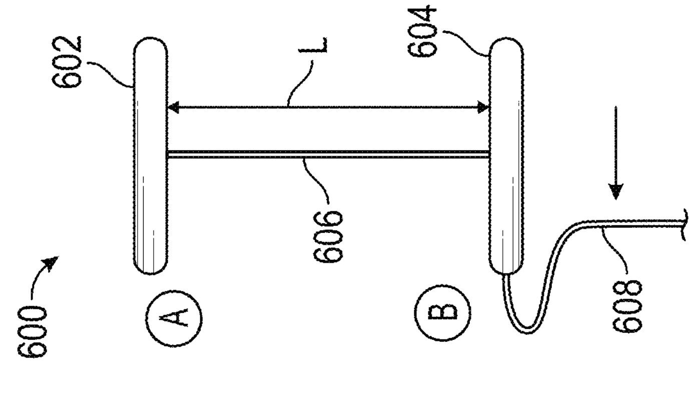

FIGS. 6A-6F illustrates methods of use of a T-Anchor assembly 600. The T-Anchor assembly 600 can have any features described herein. The T-Anchor assembly 600 can be used with any assembly described herein. The T-Anchor assembly 600 can include a first T-Anchor 602. In some embodiments, the first T-Anchor 602 can be a standard T-Anchor. The T-Anchor assembly 600 can include a second T-Anchor 604. In some embodiments, the second T-Anchor 602 can be a removable T-Anchor 604. The T-Anchor assembly 600 can include a length of suture 606 between the standard T-Anchor 602 and the removable T-Anchor 604. The T-Anchor assembly 600 can include a suture tail 608. In some embodiments, combining the standard T-Anchor 602 with the removable T-Anchor 604 can allow a ratchet-like tissue compression effect. FIG. 6A illustrates the T-Anchor assembly 600 including the standard T-Anchor 602 and the removable T-Anchor 604.

FIG. 6B illustrates delivery of the T-Anchor assembly 600. The T-Anchor assembly 600 can be implanted with both the standard T-Anchor 602 and the removable T-Anchor 604 in a bundle. The depth of the tissue can be greater than the length of suture 606 between the standard T-Anchor 602 and the removable T-Anchor 604. The length of suture 606 between the standard T-Anchor 602 and the removable T-Anchor 604 can be compressed during delivery. The T-Anchor assembly 600 can be delivered through a hollow needle 616.

FIG. 6C illustrates positioning the removable T-Anchor 604. In some methods, pulling on the suture tail 608 will straighten the removable T-Anchor 604. The removable T-Anchor 604 can be repositioned within the tissue. The removable T-Anchor 604 can be repositioned away from the standard T-Anchor 602. In some methods, pulling on the suture tail 608 will straighten the length of suture 606 between the standard T-Anchor 602 and the removable T-Anchor 604. The removable T-Anchor 604 will straighten in the direction that the suture tail 608 is pulled. The removable T-Anchor 604 can rotate counterclockwise within the tissue. The removable T-Anchor 604 is rotated from generally horizontal in FIG. 6B to generally vertical in FIG. 6C.

Figures 6D, 6E, 6F:
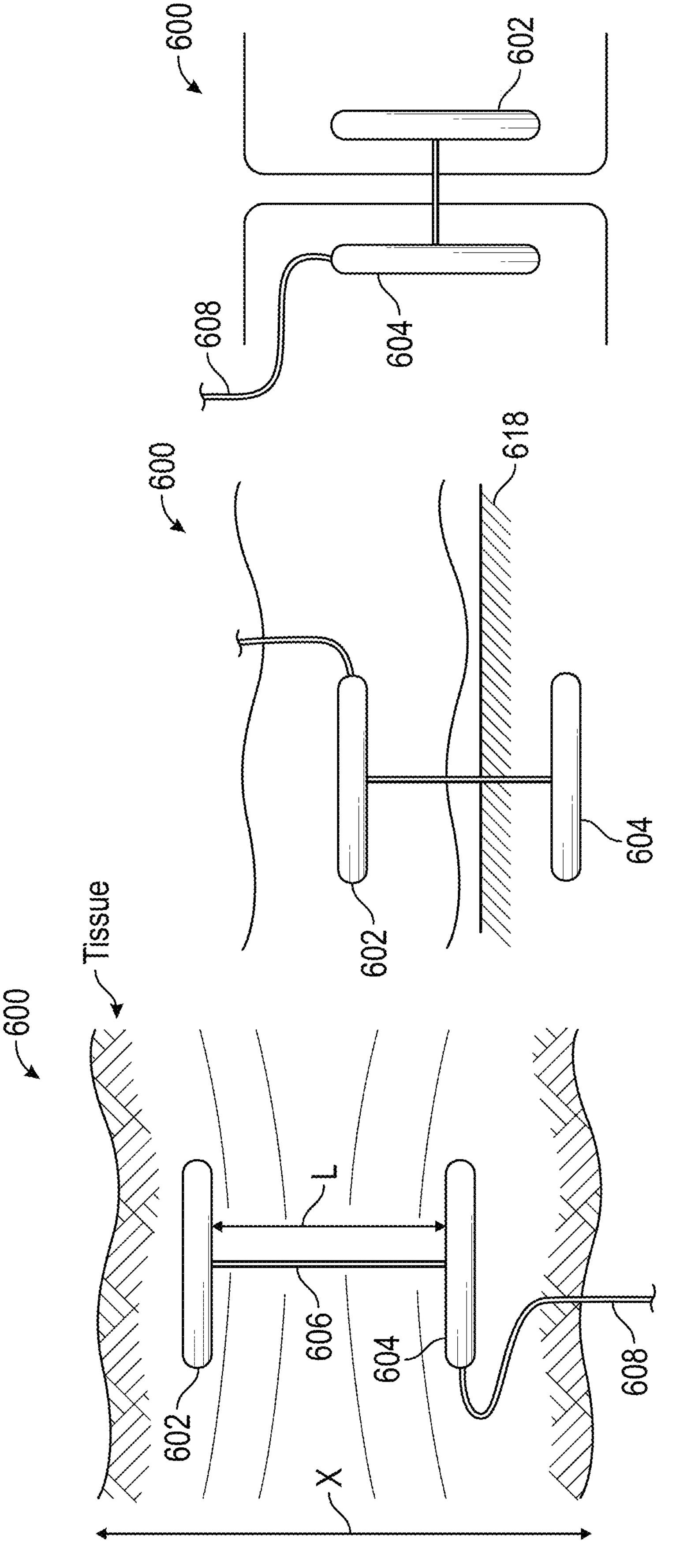

FIG. 6D illustrates the tension applied to the T-Anchor assembly 600. In some methods, continuing to pull on the suture tail 608 will cause tension in the length of suture 606 between the standard T-Anchor 602 and the removable T-Anchor 604. When the suture tail 608 is released, the tension in the length of suture 606 between the standard T-Anchor 602 and the removable T-Anchor 604 can cause the removable T-Anchor 604 to straighten. The removable T-Anchor 604 is rotated from generally vertical in FIG. 6C to generally horizontal in FIG. 6D. The tension in the length of suture 606 between the standard T-Anchor 602 and the removable T-Anchor 604 can cause the removable T-Anchor 604 to resist movement back toward the standard T-Anchor 602. The tension in the length of suture 606 between the standard T-Anchor 602 and the removable T-Anchor 604 can cause the removable T-Anchor 604 to be repositioned to compress tissue. When the suture tail 608 is released, the tension in the length of suture 606 between the standard T-Anchor 602 and the removable T-Anchor 604 can cause the removable T-Anchor 604 to be repositioned such that the removable T-Anchor 604 resists movement back toward the standard T-Anchor 602, thus compressing tissue.

FIG. 6E illustrates a use of the methods described herein. This effect of compressing tissue can be used to tack a mesh 610 for hernia repair. The mesh 610 is illustrated in FIG. 6E. When the suture tail 608 is released, the tension in the length of suture 606 between the standard T-Anchor 602 and the removable T-Anchor 604 can cause the removable T-Anchor 604 to be repositioned such that the removable T-Anchor 604 resists movement back toward the standard T-Anchor 602, thus compressing tissue and the mesh 610.

FIG. 6F illustrates a use of the methods described herein. This effect of compressing tissue can be used to help close distressed surgical wounds. When the suture tail 608 is released, the tension in the length of suture 606 between the standard T-Anchor 602 and the removable T-Anchor 604 can cause the removable T-Anchor 604 to be repositioned such that the removable T-Anchor 604 resists movement back toward the standard T-Anchor 602, thus helping to close a surgical wound. The length of suture 606 between the standard T-Anchor 602 and the removable T-Anchor 604 can span the surgical wound. The removable T-Anchor 604 can compress tissue to close the wound. The systems and methods described herein can be used for any other tissue apposition methods. The systems and methods described herein can be used for any other tissue compression methods.

Figure 7A:
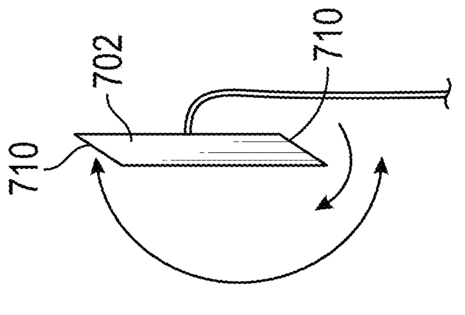
Figure 7B:
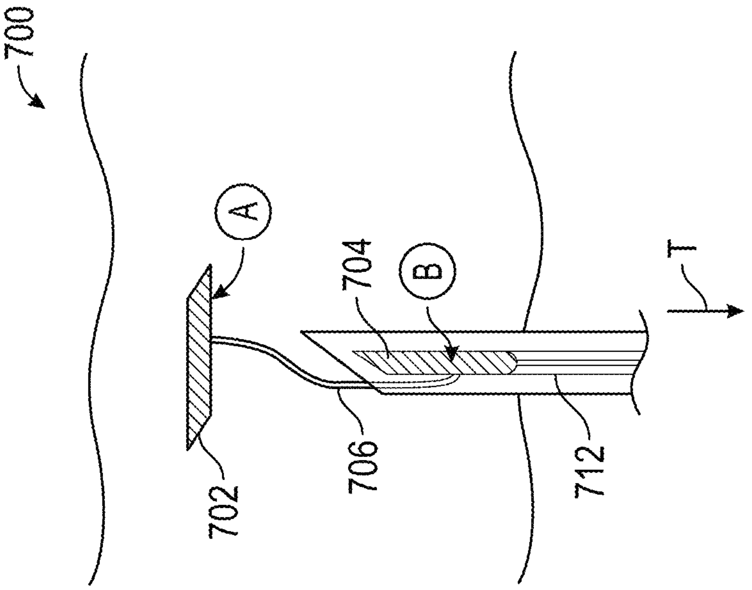
Figure 7C:
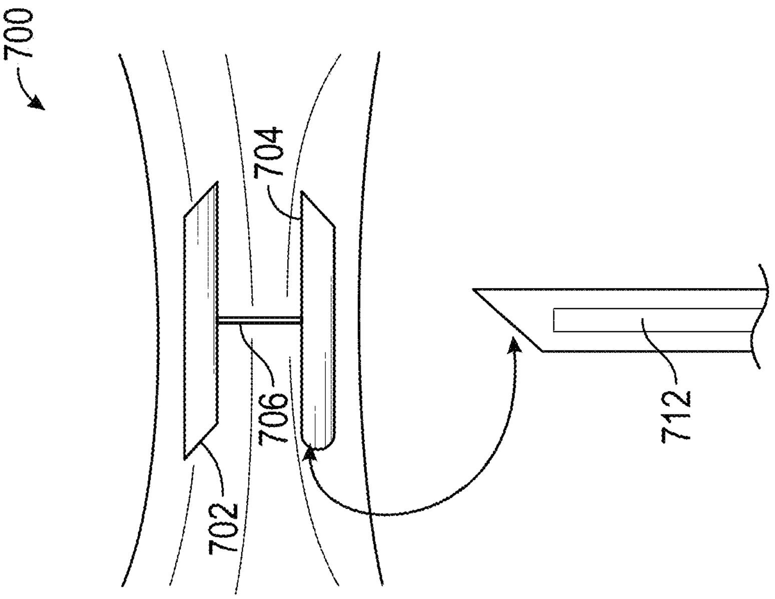

FIGS. 7A-7C illustrate a T-Anchor assembly 700. The assembly can include a T-Anchor 702. The T-Anchor 702 can have any features described herein. The T-Anchor 702 can be used with any assembly described herein. FIG. 7A illustrates the T-Anchor 702. The T-Anchor 702 can include beveled edges 702 to enhance flipping of the T-Anchor 702 to a locked position. The T-Anchor 700 can include one beveled edge 710. The T-Anchor 702 can include two beveled edges 710. The T-Anchor 702 can include any edge geometry to enhance the ability to reposition the T-Anchor 702. The T-Anchor 702 can be permanent. The T-Anchor 702 can be permeable. The T-Anchor 702 can be bioabsorable. The T-Anchor 702 can be held.

FIG. 7B shows the T-Anchor 702 as part of the T-Anchor assembly 700. The T-Anchor assembly 700 can have any features described herein. The T-Anchor assembly 700 can be used with any assembly described herein. The T-Anchor assembly can include a first T-Anchor 702 and a second T-Anchor 704. The T-Anchor assembly can include a length of suture 706 between the first T-Anchor 702 and the second T-Anchor 704. The T-Anchor assembly 700 can include a connection 712. The connection 712 can removably couple to the second T-Anchor 704. The connector 712 can be configured to apply tension before releasing the second T-Anchor 704. The connection 712 is holding the second T-Anchor 704. Tension can be applied to the length of suture 706 between the first T-Anchor 702 and the second T-anchor 704. The second T-Anchor 704 can be pulled to apply tension to the suture 706. The connection 712 can hold the T-Anchor 704 to achieve tissue compression. FIG. 7B shows tension before the release. FIG. 7C shows the release of the connection 712. The connection 712 can be released which releases the second T-Anchor 704. The second T-Anchor 704 achieves tissue compression.

Figure 8A:
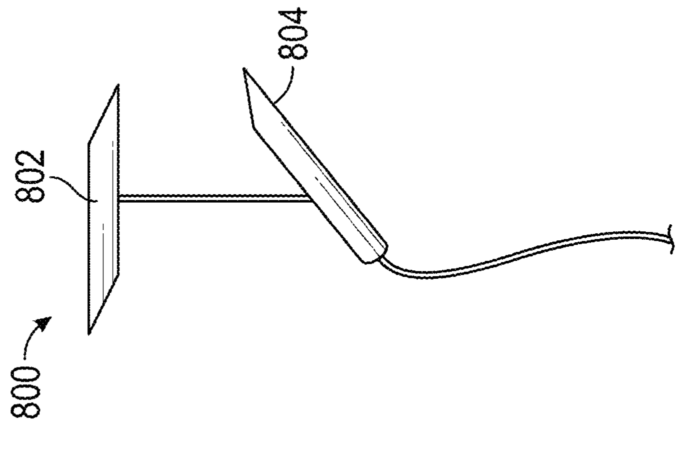
Figure 8B:
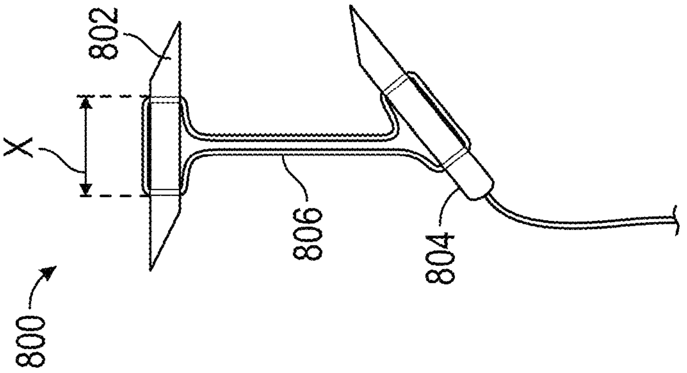
Figure 8C:
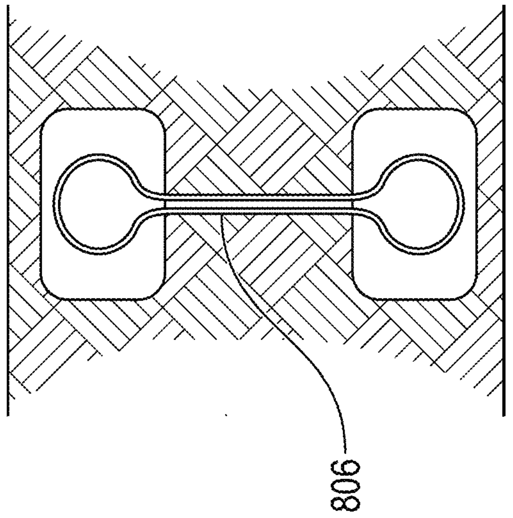

FIGS. 8A-8C illustrate a T-Anchor assembly 800. The T-Anchor assembly 800 can have any features described herein. The T-Anchor assembly 800 can be used with any assembly described herein. The T-Anchor assembly 800 can include a T-Anchor 802 and a standard T-anchor 804. FIG. 8A illustrates that the T-Anchor assembly 800 can include a standard ratchet. FIG. 8B illustrates that the T-Anchor assembly 800 can include a looped suture ratchet. The standard T-anchor 802 can be made of any material. In some embodiments, the standard T-anchor 802 bioresorbs. In some embodiments, the standard T-anchor 802 comprises PLA or PLLA. The T-anchor 804 can be made of any material. In some embodiments, the T-anchor 804 bioresorbs. In some embodiments, the T-anchor 804 comprises PLA or PLLA. The T-Anchor assembly 800 can include a looped suture 806. In some embodiments, the looped suture 806 is permanent. The looped suture 806 can remain in the tissue after the resorption of the T-Anchor 802 and the standard T-anchor 804. The looped suture 806 can extend along a length of the T-Anchor 802 and the standard T-anchor 804. The looped suture 806 can increase the surface area of attachment of the suture to tissue. The looped suture can allow better attachment to tissue after healing and resorption of the T-Anchor 802 and the standard T-anchor 804. FIG. 8C illustrates the looped suture 806 in the fibrous tissue post healing. The looped suture 806 can be permanent.

Figure 9A:
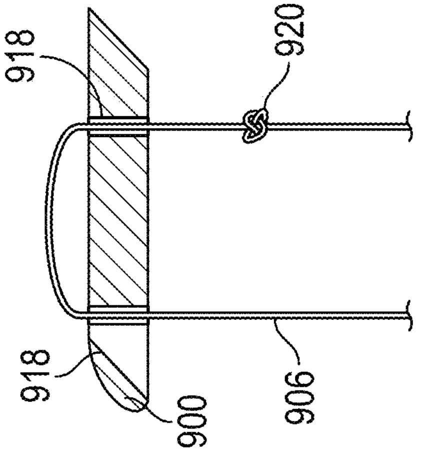
Figure 9B:
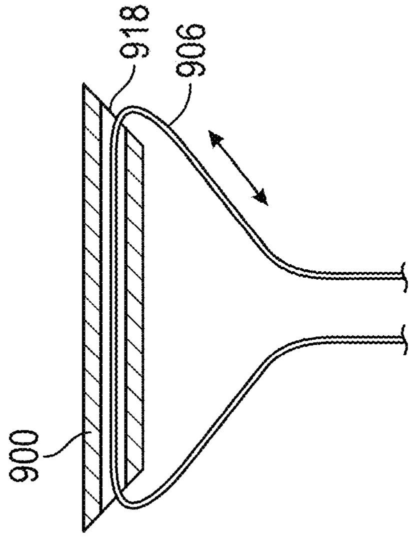
Figure 9C:
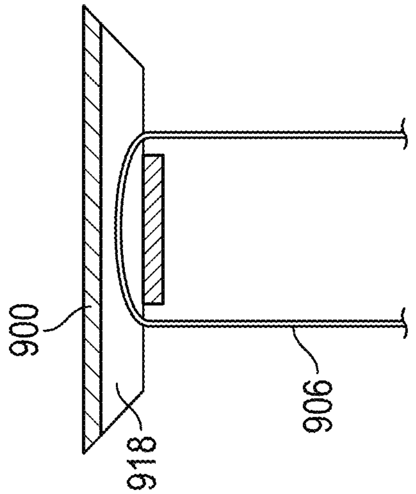

FIGS. 9A-9C illustrate a T-Anchor 900. The T-Anchor 900 can have any features described herein. The T-Anchor 900 can be used with any assembly described herein. If the T-Anchor 900 is bioresorbable, the system will leave a loop of suture 902 healed to tissue. The T-Anchor 900 can include a slot 918. The T-Anchor 900 can include one or more slots 918 to receive the suture 906. The suture 902 can include a knot 920. The knot 920 can be larger in diameter that the slot 918 to prevent the suture 906 from sliding in one direction. The suture 906 can be flexible. The suture 906 can be slideable. The suture 906 can be fixed. FIG. 9A illustrates the T-Anchor 900 with an embodiment of a slot configuration. FIG. 9B illustrates another slot configuration. The suture 906 can be slidable FIG. 9C illustrates another slot configuration.

Figure 10C:
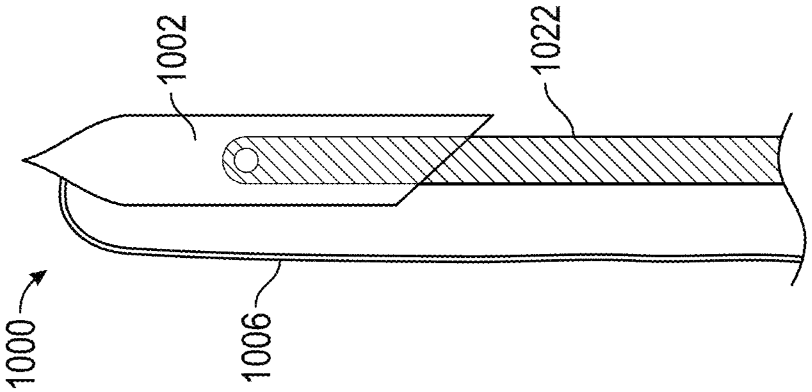
Figure 10B:
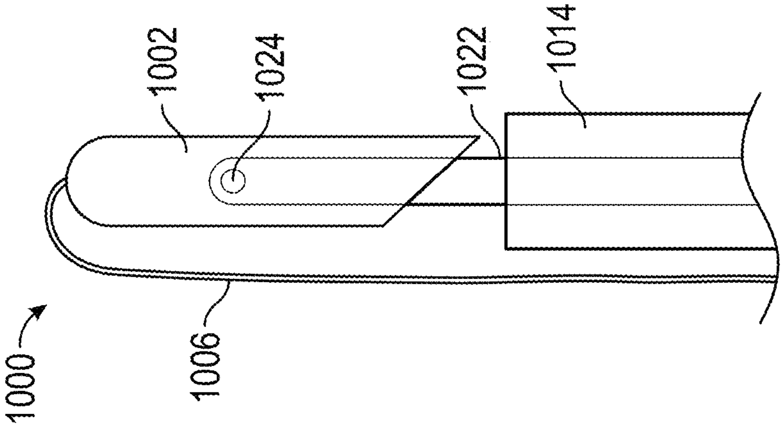
Figure 10A:
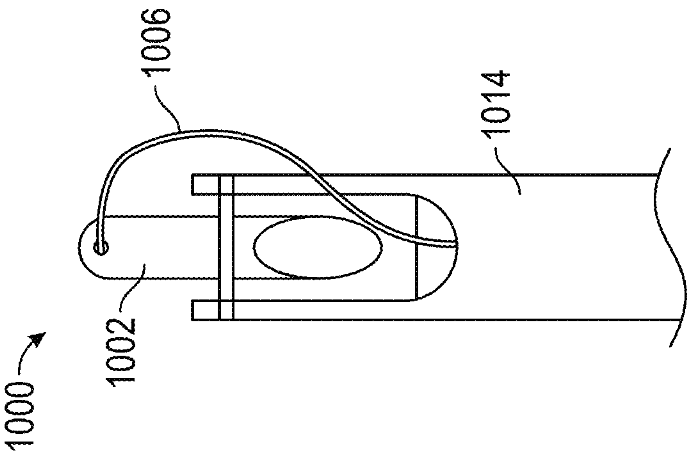

FIGS. 10A-10C illustrate a T-Anchor assembly 1000. The T-Anchor assembly 1000 can have any features described herein. The T-Anchor assembly 1000 can be used with any assembly described herein. The T-Anchor assembly 1000 can include a T-Anchor 1002 and a suture 1006. The suture 1006 can connected to the T-Anchor 1002. The T-Anchor assembly 1000 can be delivered with a delivery tool 1014. The delivery tool 1014 can include a rigid member 1022. The delivery tool 1014 can include a hypotube. The T-Anchor assembly 1000 can include a hinge 1024. The hinge 1024 can be between the T-Anchor 1002 and the rigid member 1022. The suture 1004 can be flexible. The delivery tool 1006 can be non-flexible.

Figure 11:
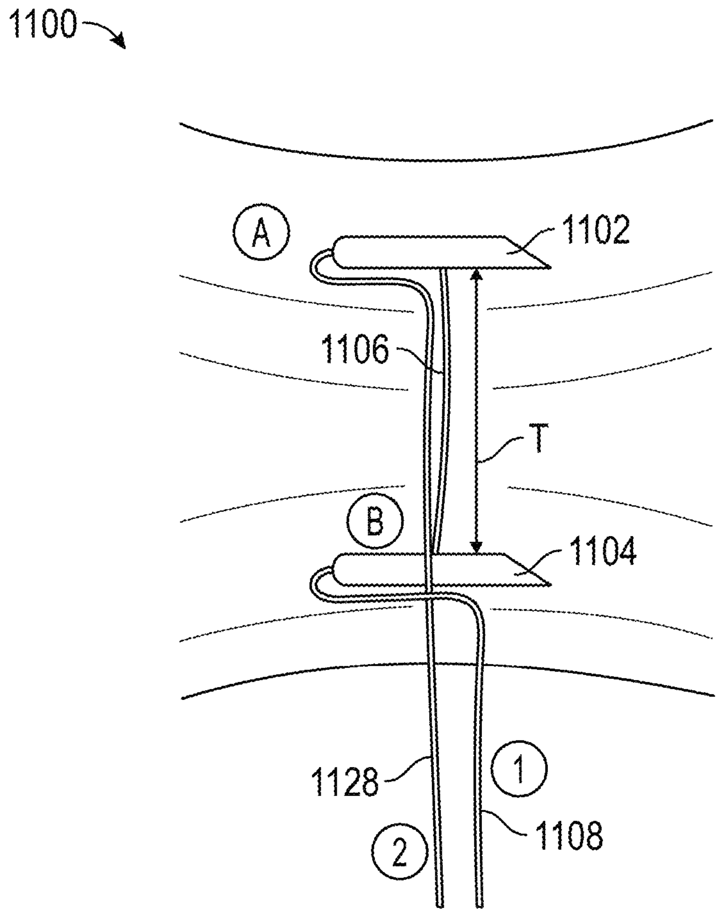

FIG. 11 illustrates a T-Anchor assembly 1100. The T-Anchor assembly 1100 can have any features described herein. The T-Anchor assembly 1100 can be used with any assembly described herein. The T-Anchor assembly 1100 can include a first T-Anchor 1102. The T-Anchor assembly 100 can include a second T-Anchor 1104. The T-Anchor assembly 1100 can include a length of suture 1106 between the first T-Anchor 1102 and the second T-Anchor 1104. The T-Anchor assembly 1100 can include a suture tail 1108. The suture tail 1108 can be coupled the second T-Anchor 1104. The T-Anchor assembly 1100 can include a suture tail 1128. The suture tail 1128 can be coupled the first T-Anchor 1102. The T-Anchor assembly 1100 can include a removable ratchet anchor.

In some methods, pulling on the suture tail 1108 connected to the second T-Anchor 1104 increases the tension on the length of suture 1106 between the first T-Anchor 1102 and the second T-Anchor 1104. In some methods, pulling on the suture tail 1128 connected to the first T-Anchor 1102 reduces tension on the length of suture 1106 between the first T-Anchor 1102 and the second T-Anchor 1104. In some methods, pulling on the suture tail 1128 connected to the first T-Anchor 1102 only reduces tension by repositioning the first T-Anchor 1102. In some methods, pulling on both the suture tail 1108 connected to the second T-Anchor 1104 and the suture tail 1128 connected to the first T-Anchor 1102 removes the entire assembly. In some embodiments, the suture tail 1128 connected to the first T-Anchor 1102 and the suture tail 1108 connected to the second T-Anchor 1104 can be provided to make the entire assembly removable.

In some embodiments, multi-element anchors are provided. The following embodiments and those described herein illustrate multi-element anchors that facilitate anchoring in soft tissue. The embodiments incorporate two individual anchor elements connected by a flexible member thus allowing for significant relative movement/rotation between them. The specific path the flexible element takes through the individual elements can enhance rotational movement of the anchoring elements when tension is applied to the flexible element. This effect can enhance the initial anchoring of the elements into soft tissue by increasing the distance between the tips of the anchoring elements and more aggressively engaging the soft tissue.

In some embodiments, the systems and methods use elements attached together with a flexible element to enhance expansion and engagement with tissue while maintaining a low delivery profile compared with typical barbs. In some embodiments, there can be greater expanded size to delivery size ratio. In some embodiments, the systems and methods use tension in the suture to actively expand elements. In some embodiments, the systems and methods maintain removability of the anchors by having a suture attached to the distal end of the distal anchor. When the distal suture is pulled proximally, the anchor repositions itself into an orientation that facilitates removal from the soft tissue. In some embodiments, as opposed to the typical T-Anchors which do not reliably anchor within tissue at the delivered site, the systems and methods described herein can actively engage tissue for secure and precise anchoring. T-Anchors are better suited to anchor to the edge of a tissue interface and not within tissue.

Figure 12A:
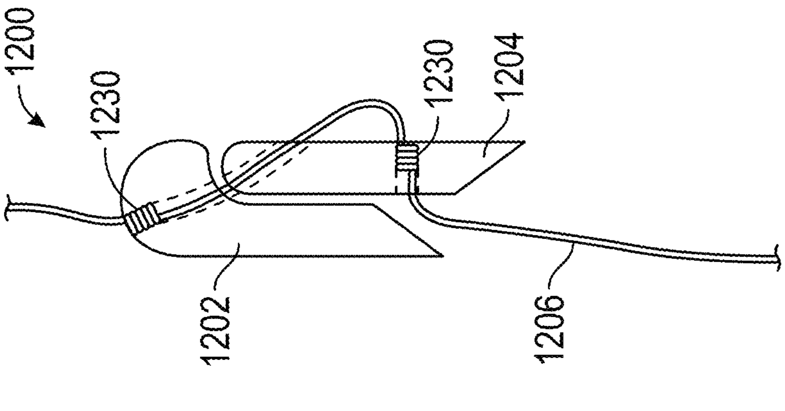
Figure 12B:
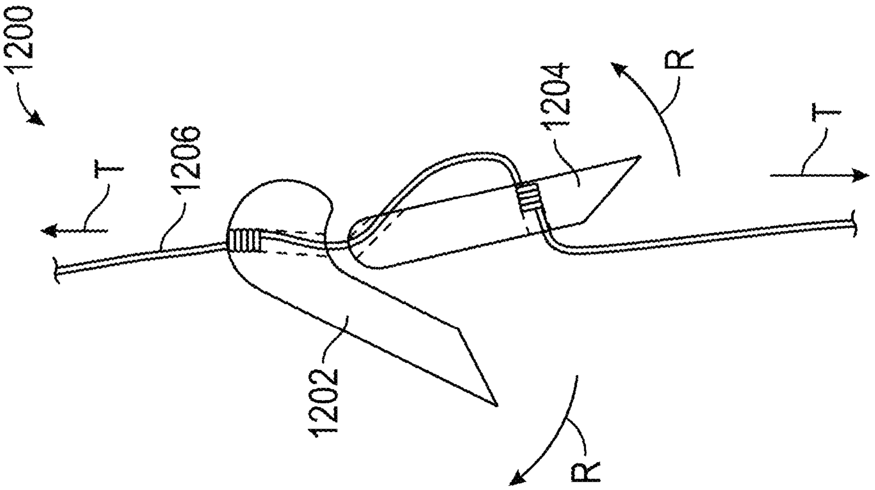
Figure 12C:
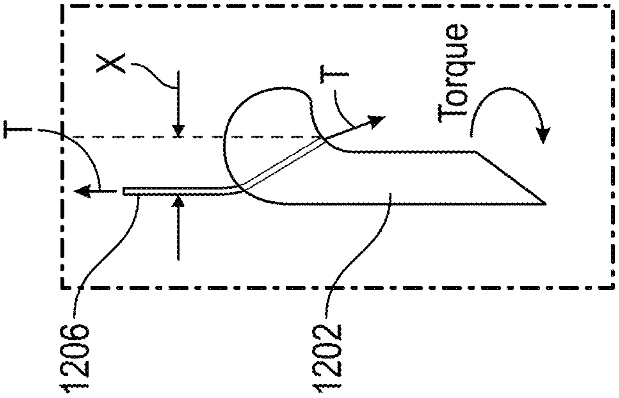

FIGS. 12A-12C illustrate an anchoring assembly 1200. The anchoring assembly 1200 can have any features described herein. The anchoring assembly 1200 can be used with any assembly described herein. The anchoring assembly 1200 can include a first element 1202 and a second element 1204. The anchoring assembly 1200 can include a suture 1206. The suture 1206 can extend through the first element 1202. The suture 1206 can extend through the second element 1204. FIG. 12A illustrates the suture bond points 1230. In some embodiments, the suture bond points 1230 can fixedly attach the suture 1206 to the first element 1202 and the second element 1204. In some embodiments, the suture body points can define the length of suture between the first element 1202 and the second element 1204. FIG. 12A illustrates no tension. FIG. 12B illustrates the application of tension on the suture 1206. The first element 1202 can rotate clockwise as the tension is applied. The first element 1202 can rotate counterclockwise as the tension is applied. FIG. 12C illustrates anchor expansion with tension. Due to the torque applied to the first element 1202 and the second element 1204 the anchor assembly 1200 can expand. Anchor expansion can be caused by tension applied over orthogonal distance. Torque can equal the tension multiplied by the distance.

Figure 13A:
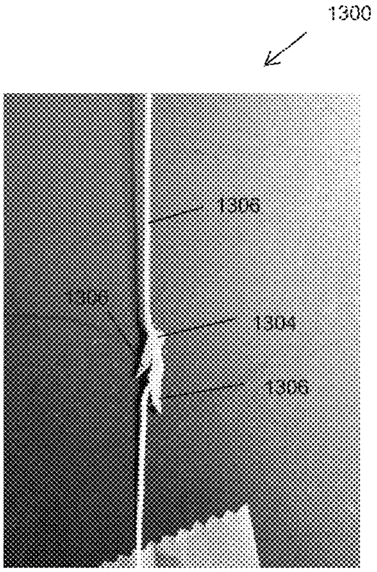
Figure 13B:
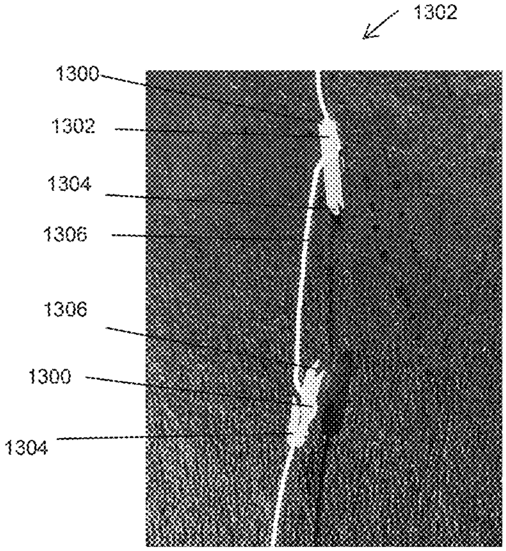

FIG. 13A illustrates an embodiment of a single anchor 1300. The anchor 1300 can have any features described herein. FIG. 13B illustrates an embodiment of an anchor assembly 1302 used for tissue compression. In some embodiments, the anchoring assembly 1302 comprises two anchors 1300. The anchoring assembly 1300 can have any features described herein. The anchoring assembly 1300 can be used with any assembly described herein. The anchor 1300 can include a body 1304. The anchor 1300 can include one or more barbs 1306. The barbs 1306 can laterally extend from the body 1304. The barbs 1306 can be laterally opposed. The barbs 1306 can be axially offset. The barbs 1306 can have any configuration to engage tissue. The anchoring assembly 1302 can include a first anchor 1300 and a second anchor 1300. The anchor 1300 and the anchoring assembly 1302 can include a suture 1306. The first anchor 1300 and the second anchor 1300 can be spaced apart along the suture 1306. Tension can be applied to the suture and then released as described herein. The barbs can engage tissue similar to the beveled edges described herein. The anchor assembly 1300 can be used for tissue compression.

Figure 14A:
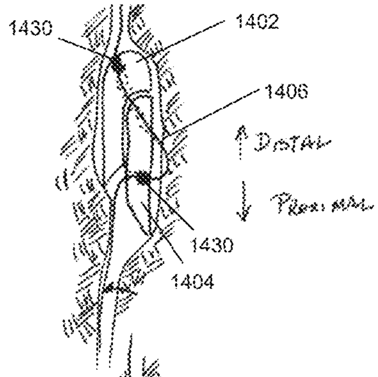
Figure 14B:
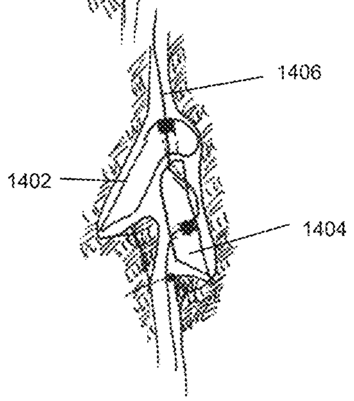

FIGS. 14A-14B illustrate an embodiment of anchoring assembly 1400. The anchoring assembly 1400 can have any features described herein. The anchoring assembly 1400 can be used with any assembly described herein. The anchoring assembly 1400 can include a first element 1402 and a second element 1404. The anchoring assembly 1400 can include a suture 1406. FIG. 14A illustrates the anchoring assembly 1400 without tension. The suture bond points 1430 are shown. The suture extends along a suture path through the tissue. FIG. 14B illustrates the anchoring assembly 1400 with tension. The first element 1402 can rotate. The first element 1402 can pivot. The first element 1402 can dig into tissue. The second element 1404 can rotate. The second element 1404 can pivot. The second element 1404 can dig into tissue. The first element 1402 can include one or more edges to facilitate gripping the tissue. The second element 1404 can include one or more edges to facilitate gripping the tissue. The anchor engagement is shown in FIG. 14B.

Figure 15A:
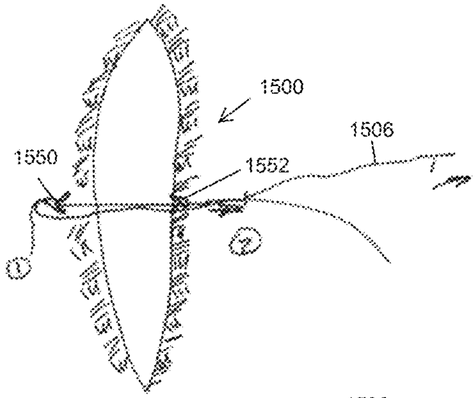
Figure 15B:
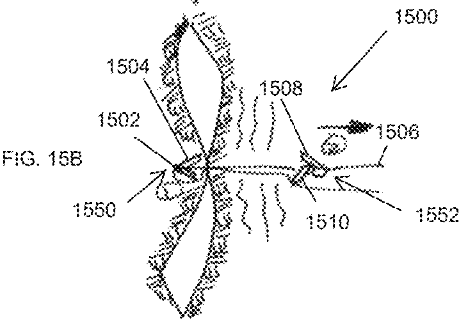

FIGS. 15A-15B illustrate wound closure. FIG. 15A illustrates the wound in tissue. FIGS. 15A-15B illustrate an embodiment of anchoring assembly 1500. The anchoring assembly 1500 can have any features described herein. The anchoring assembly 1500 can be used with any assembly described herein. The anchoring assembly 1500 can include a first element 1502 and a second element 1504. The anchoring assembly 1500 can include a suture 1506. The anchoring assembly 1500 can include a third element 1508 and a fourth element 1510. The first element 1502 and the second element 1504 can form a first multi-element anchor 1550. The third element 1508 and the fourth element 1510 can form a second multi-element anchor 1552. In some embodiments, pulling the second multi-element anchor can cause the first multi-element anchor 1550 to slip through tissue and anchor in new position, thus compressing tissue between the first multi-element anchor 1550 and the second multi-element anchor 1552. Tension can be applied to the suture 1506. FIG. 15B illustrates the wound is closed due to tissue compression the first multi-element anchor 1550 and the second multi-element anchor 1552. FIG. 15B shows this compression. This effect can be used to close wounds. This effect can be used reposition tissue. This effect can be used to reposition the tongue. This effect can be used to reposition the palate. This effect can be used stabilize other implants like hernia mesh against tissue. This effect can be used for emergency deep tissue compression for managing bleeding. This effect can be used emergency deep tissue compression trauma. This effect can be used cosmetic applications.

Figure 16:
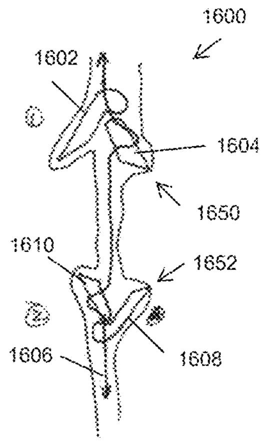

FIG. 16 illustrates the ratchet effect. FIG. 16 illustrate an embodiment of anchoring assembly 1600. The anchoring assembly 1600 can have any features described herein. The anchoring assembly 1600 can be used with any assembly described herein. The anchoring assembly 1600 can include a first element 1602 and a second element 1604. The anchoring assembly 1600 can include a suture 1606. The anchoring assembly 1600 can include a third element 1608 and a fourth element 1610. The first element 1602 and the second element 1604 can form a first multi-element anchor 1650. The third element 1608 and the fourth element 1610 can form a second multi-element anchor 1652.

In some embodiments, pulling the first multi-element anchor 1650 can cause the first multi-element anchor 1650 anchor to slip through tissue and anchor in new position, thus compressing tissue between the first multi-element anchor and the second multi-element anchor. In some embodiments, pulling the second multi-element anchor 1652 can cause the second multi-element 1652 anchor to slip through tissue and anchor in new position, thus compressing tissue between the first multi-element anchor and the second multi-element anchor. This effect can be used to close wounds. This effect can be used reposition tissue. This effect can be used to reposition the tongue. This effect can be used to reposition the palate. This effect can be used stabilize other implants like hernia mesh against tissue. This effect can be used for emergency deep tissue compression for managing bleeding. This effect can be used emergency deep tissue compression trauma. This effect can be used cosmetic applications.

Figure 17A:
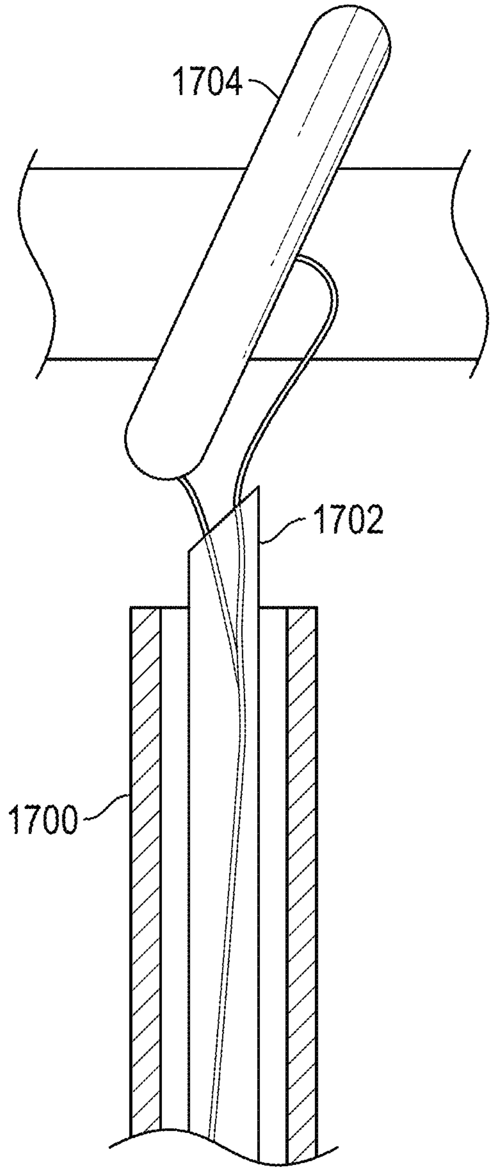
Figure 17B:
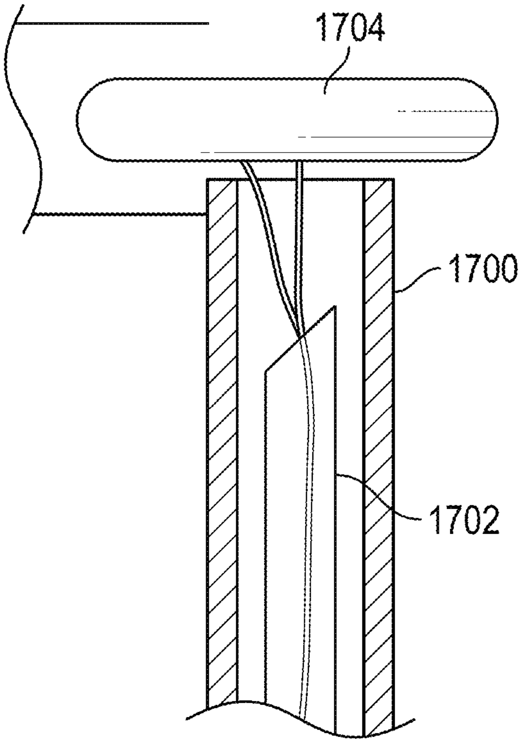

FIGS. 17A-17B illustrate the use of a sheath 1700 over a delivery needle 1702. The distal anchor 1704 is deployed in the manner described herein as shown in FIG. 17A. After the distal anchor 1704 is deployed in the manner described herein, the sheath 1700 can slid forward to engage and rotate and seat the distal anchor 1704 at the point of deployment as shown in FIG. 17B. The sheath 1700 can enhance the ability to seat the distal anchor 1704 at the point where the distal anchor 1704 was deployed. The sheath 1700 and method of use may be advantageous if there is a narrow band of tissue where the user intends to place the anchor 1704. The sheath 1700 and method of use can minimize the displacement of the anchor 1704 before it seats within the tissue.

Any element, anchor, multi-element anchor, anchoring assembly, T-Anchor, standard, and/or T-anchor can be utilized in any systems or methods. The elements of the embodiments can be combined into various combinations and sub combinations.

Various other modifications, adaptations, and alternative designs are of course possible in light of the above teachings. Therefore, it should be understood at this time that the inventions may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described. Any methods disclosed herein need not be performed in the order recited. The methods disclosed herein include certain actions taken by a practitioner; however, they can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A system comprising:
a first T-Anchor;
a second T-Anchor; and
a length of suture between the first T-Anchor and the second T-Anchor, wherein applying and releasing tension to the second T-Anchor allows for tissue compression or apposition, wherein the first T-Anchor is configured to rotate clockwise and the second T-Anchor is configured to rotate counterclockwise when tension is applied.

2. The system of claim 1, wherein at least one T-Anchor comprises blunt end.

3. The system of claim 1, wherein at least one T-Anchor comprises beveled edge.

4. The system of claim 1, further comprising a connector between a delivery system and the second T-Anchor, wherein the delivery system is configured to apply tension before release of the second T-Anchor.

5. The system of claim 1, wherein the second T-Anchor has a suture tail configured to reposition the second T-Anchor when tension is applied.

6. The system of claim 1, wherein the second T-Anchor has a suture tail configured to lock the second T-Anchor when tension is released.

7. The system of claim 1, wherein the first T-Anchor has a suture tail to reposition the first T-anchor.

8. The system of claim 1, wherein the first T-Anchor and the second T-Anchor each have a suture tail to remove the first T-Anchor and the second T-Anchor.

9. The system of claim 1, wherein at least one T-Anchor is bioresorbable.

10. A method comprising:
positioning a first T-Anchor within tissue;
positioning a second T-Anchor within tissue; and
applying and releasing tension to the second T-Anchor for tissue compression or apposition within tissue.

11. The method of claim 10, wherein the method does not require tying knots.

12. The method of claim 10, wherein the method is for permanent anchoring.

13. The method of claim 10, wherein the method is for temporary anchoring.

14. The method of claim 10, wherein applying and releasing tension to the second T-Anchor for tissue compression or apposition further comprises tacking a mesh for hernia repair.

15. The method of claim 10, wherein applying and releasing tension to the second T-Anchor for tissue compression or apposition further comprises closing a wound.

16. A system comprising:

a first element;

a second element; and a fixed length of a suture between the first element and the second element, wherein a first suture bond point fixedly attaches the suture to the first element and wherein a second suture bond point fixedly attaches the suture to the second element, wherein applying and releasing tension to at least one element allows for relative movement and/or rotation between the first element and the second element.

17. The system of claim 16, wherein the relative movement and/or rotation between the first element and the second element is configured to enhance the initial anchoring of the system.

18. The system of claim 16, wherein at least one element comprises a beveled tip.

19. The system of claim 16, wherein the suture extends through the first element and the second element.

20. The system of claim 16, wherein the first element is configured to rotate clockwise and the second element is configured to rotate counterclockwise when tension is applied.

* * * * *